United States Patent [19]

Clark et al.

[11] 4,220,162
[45] Sep. 2, 1980

[54] ALVEOLAR GAS SAMPLING SYSTEM AND METHOD

[75] Inventors: Justin S. Clark; Frederick L. Farr, both of Salt Lake City, Utah

[73] Assignee: Intermountain Health Care

[21] Appl. No.: 963,393

[22] Filed: Nov. 24, 1978

Related U.S. Application Data

[63] Continuation-in-part of Ser. No. 636,357, Dec. 1, 1975, abandoned.

[51] Int. Cl.³ .............................................. A61B 5/08
[52] U.S. Cl. .................................... 128/724; 128/719; 128/730
[58] Field of Search ....................... 128/719, 724, 730; 73/421.5 R

[56] References Cited

U.S. PATENT DOCUMENTS

| | | | |
|---|---|---|---|
| 3,395,701 | 8/1968 | Bartlett, Jr. et al. ................. | 128/719 |
| 3,509,771 | 5/1970 | Moberg et al. ....................... | 128/719 |
| 3,613,665 | 10/1971 | Gorsuch ............................... | 128/730 |
| 3,661,528 | 5/1972 | Falk ................................ | 73/421.5 R X |
| 3,910,261 | 10/1975 | Ragsdale ............................. | 128/719 |
| 3,927,670 | 12/1975 | Turney et al. ....................... | 128/719 |

Primary Examiner—Kyle L. Howell
Attorney, Agent, or Firm—Criddle & Western

[57] ABSTRACT

An alveolar gas sampling system comprises a catheter adapted for placement in a patient's nostril or in an endotracheal tube and connected to a positive displacement pump through a three way valve. Signal means for detecting onset of inspiration and expiration is mounted at the tip of the catheter and connected to a controller. The positive displacement pump is driven by a reversible stepper motor actuated by the controller during the flow of alveolar air. When the desired amount of alveolar gas has been sampled, the stepper motor is reversed and the position of the valve is switched by the controller causing the alveolar gas collected in the positive displacement pump to be expelled for analysis.

4 Claims, 2 Drawing Figures

ALVEOLAR GAS SAMPLING SYSTEM AND METHOD

BACKGROUND OF THE INVENTION

This application is a continuation-in-part of Ser. No. 636,357 filed Dec. 1, 1975 now abandoned.

This invention is related to a method of alveolar gas sampling. More particularly, this invention relates to method and apparatus for alveolar gas sampling by withdrawing alveolar gas through a simple catheter placed in the tip of a patient's nostril, an endotracheal tube or endotracheal tube connector by a positive displacement pump driven by a reversible stepper motor.

Alveolar gas sampling devices are known in the art, however, such devices consist of non-rebreathing valves with tubes attached to the expiratory port which is interfaced to a patient using a mask or mouthpiece. A reservoir is mounted on the expiratory tube and fills with gas from which samples are drawn. Other devices are dependent upon solenoid valves which are sluggish and are often not reliable.

Moreover, a particular problem develops in attempting to sample alveolar gas from an infant since conventional methods for pulmonary function testing require extensive verbal instruction from the technician conducting the test and considerable cooperation by the patient. Such tests also occasionally subject the patient to some discomfort. For these reasons it is difficult to perform these tests in infants and small children. The necessary verbal instruction is not understood by small children who will seldom tolerate even minor physical discomfort. In the past, because of these difficulties, extensive pulmonary function testing is seldom done on children, and other tests which require less cooperation, but which are also less quantative are used to diagnose the large number of respiratory illnesses of babies and small children.

OBJECTS OF THE INVENTION

It is an object of the present invention to create a system which makes possible routine clinical alveolar gas sampling in infants and adults.

It is a further object of the present invention to provide a practical alveolar gas sampling system for infants wherein a non-invasive catheter is used and alveolar gas is collected through said catheter by means of a positive displacement pump driven by a reversible stepper motor.

It is also an object of this invention to provide a system capable of sampling a variable portion of expiration gas in order to obtain a more nearly "mean alveolar" gas sample.

The principal features of this invention include an alveolar gas sampling system wherein the gas samples are drawn through a catheter into a positive displacement pump during the latter part of the expiration cycle. A catheter tip may be placed in the patient's nostril, in an endotracheal tube, or in an endotracheal tube connector. A temperature responsive thinistor (thin film thermistor with a frequency response much faster than the smallest bead type) or other signal means is mounted at the tip of the catheter and its signal is transmitted to a controller which in turn operates the reversible stepper motor and a valve for directing the flow of gas into and out of the positive displacement pump. This reversible stepper motor, which drives the pump, can start, stop or reverse within about three to ten milliseconds. The pump contents are emptied after the collection of a predetermined amount of gas. The collected gas is pushed into either a larger glass syringe for later insertion into an analyzer or directly into the analyzer wherein the partial pressures of the various gasses can be measured.

DRAWINGS OF THE INVENTION

DETAILED DESCRIPTION OF THE INVENTION

Figure 1:
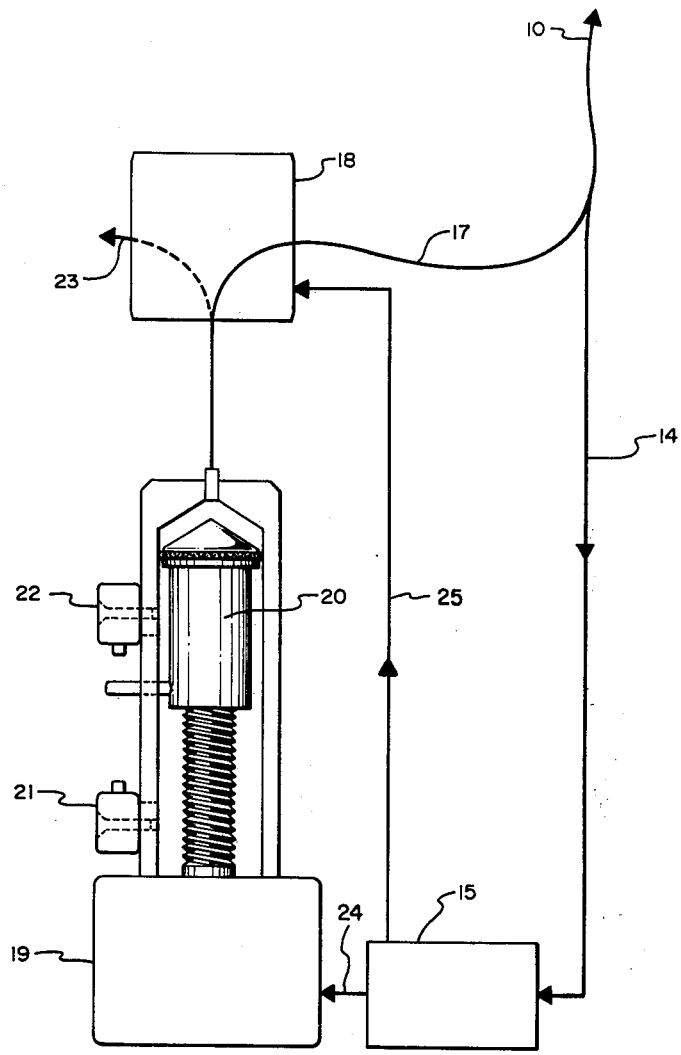
FIG. 1 is a schematic view of the gas sampling system.
Figure 2:
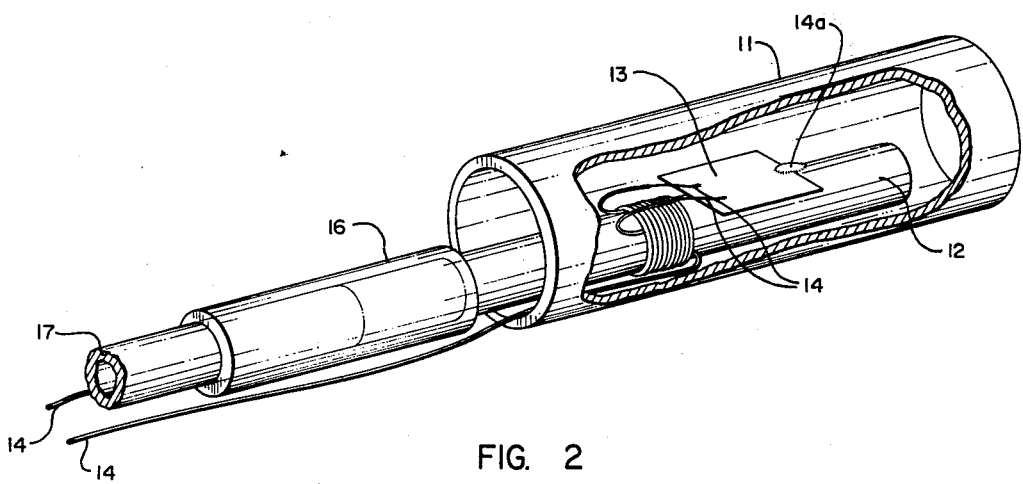
FIG. 2 is a partially cut-away view of the tip of the gas sampling catheter showing the thermistor mounting.

Referring now to the Drawings:

There is shown in FIGS. 1 and 2 an operative embodiment of the invention, the novel features of which will be described hereinafter. One of the major advantages of the present invention is that the gas collection and gas analysis functions are separated or may be separated so that one central analyzer can or may service many patients. This reduces overall expense, maintenance, and bulk as well as removes the necessity of having analyzers at each patient's bedside. A second distinct advantage of the invention is that the system will interface conveniently to non-cooperative infants and children, some of whom are obligatory nose breathers. These patients may be breathing inside headboxes or they may be interfaced to respiratory assist devices via endotracheal tubes. As will be further described, a key feature of the invention is the control of the sampling process by means of a positive displacement pump driven by a reversible stepper motor coupled with the fact that the system is designed to sample expired gas over a number of respiratory cycles producing a time averaged alveolar gas sample. The system is economical and utilizes a catheter which is encumbered only by a small temperature responsive thermistor or other signal means which allows the system to be easily interfaced to patients under a variety of circumstances.

There is schematically illustrated in FIG. 1, a catheter 17 which is attached to a patient. The catheter tip 10 is more specifically illustrated in FIG. 2 and comprises a thermistor guard 11 adapted to fit into the nostril or endotracheal tube of a patient. The thermistor guard, as illustrated, is partially cut-away to illustrate the catheter tip 12 to which is mounted a thermistor 13. The thermistor guard 11 is small, and as such, does not completely block the air passageway into the nostril. The catheter tip likewise is small in size. The temperature responsive thinistor (thin film thermistor) is mounted at the tip of the catheter as illustrated and secured by welding or adhesive means 14a. Connected to thermistor 13 are signal responsive means 14 which are connected to a controller 15 as illustrated in FIG. 1. The catheter tip 10 may be connected to a catheter 17 by a connecting sleeve 16 as illustrated in FIG. 2. Catheter 17 leads to a three-way valve 18 at its other end. The controller 15 is responsive to the respiratory cycle of the patient and is so designed to operate a reversible stepper motor 19 and three way valve 18 in the sampling of alveolar gas. Typical of controllers and stepper motors for use in the present invention are those manufactured by IMC Magnetics Corporation under the trade name "Tormax". Tormax Stepper Motor, Model No. 020-010 and IMC Controller, Model No. 0128 50 3312-01 are particularly adaptable.

The gas sampling system eliminates the need for solenoid valves and the like by the use of a fast responding motor 19 connected to controller 15 which drives a positive displacement pump 20, thus allowing the sampling process to be controlled by the pump itself. The motor is preferably a stepper motor operated by digital pulses which are supplied at a fixed rate. e.g., about 300 per second which results in a constant volume displacement rate in the pump chamber, for example, about one cc per second. This volumetric control results in a stable gas flow eliminating the uncertainties and need for adjustment that exist when flow is regulated by pressure differences and line resistances.

The ability of the stepper motor 19 to reverse makes possible the expulsion of unwanted gas samples. The length of the catheter from the patient to the three-way valve may be on the order of about three feet and have a reservoir capacity of about 0.4 cc. This constitutes a purgable gas reservoir from which the gas can be expelled through the catheter before it contaminates the sample collected in the pump itself. The ability of this system to expel gas allows sampling to continue until the onset of inspiration is detected. The pump is then reversed to expel the last part of the sample through the catheter. There is thus no need for sampling to be timed to cease before the end of expiration to avoid contamination by inspired air as is the case in prior art samplers.

The digital nature of stepper motors precludes the time delays in the response of such motors; therefore, if the pump is observed to be moving (the pump chamber is preferably transparent), it can be assumed that it is functioning correctly. By contrast, most solenoid valve operations are invisible and sluggish operation of such valves is difficult, if not impossible to detect.

The sampling procedure allows the averaging of alveolar gas from several respiratory cycles. The pump collects an average of about 0.5 to 1.0 cc of gas before emptying; this usually requires sampling over two or more respiratory cycles in sick infants. Pump volume is only checked at the end of expiration. However, the setting of limit switches 21 and 22 at a predetermined volume, such as one cubic centimeter, provides adequate room for over-run so that the sampling process does not stop during the expiration. After the collection of a predetermined amount of alveolar gas the three-way valve 18 is activated by controller 15 closing off catheter 17 and the gas sample is pushed through an inter connecting tube 23 either to a collection chamber such as a glass syringe or directly to an analyzer. Collection of the gas allows further time averaging of alveolar gas since, for example, a total of about twenty-four 0.5–1 cc samples (collected over a two to three minute period) are obtained. When the samples are pushed directly to the analyzer (in series), some of this time averaging is sacrificed. The gas samples may be analyzed by a suitable means such as a mass spectograph or by electrodes which measure the partial pressure of gases.

FIG. 2 shows the mounting of the thermistor 13 near the catheter tip. The fast responding thermistor, for example, response time 0.1 to 0.5 millisecond is protected by a cylindrical guard 11, of suitable material such as aluminum. The deadspace of the small catheter tip assembly is small such as 0.1 cc and it can be easily inserted into an endotracheal tube or endotracheal tube connector. If the patient does not have an endotracheal tube, the catheter tip assembly is first inserted into a tapered adapter (not shown) which is then placed in the patient's nostril. The small adapter used for newborn infants, for example, adds only 0.1 cc of deadspace.

The means for detecting the onset of flow of alveolar air are well known in the art. The use of a thermistor is illustrated because of its size and convenience in being mounted in the tip of catheter 10. The onset of expiration is noted by a warming of thermistor 13 by exhaled air. The sampling operation is programmed to take place in late expiration after washout of the anatomical deadspace has occurred. This may be accomplished by methods well known in the art such as sampling when exhaled air reaches a temperature plateau or beginning sampling at a predetermined time after the onset of expiration has been detected by thermistor 13 followed by a preset sampling period. If for any reason, inspiration begins before the end of a predetermined sampling period, the cooling of thermistor 13 by inhaled air is immediately relayed to controller 15 causing motor 19 to stop and sampling to cease. Motor 19 is then caused to reverse momentarily to eliminate the contaminant of inhaled gas which enters the sampling catheter so inspiration is detected.

The controller receives signals from the thermistor 13 and controls the operation and direction of stepper motor 19 and the positioning of valve 18 by means of a control algorithm which does not form a part of this invention. It is the incorporation of a positive displacement pump operated by a reversible stepper motor into the sampling system which allows direct sampling of alveolar gas that forms the invention and not the particular means or method used in determining when to begin and stop sampling.

In a typical method of operation a non-invasive catheter 10 is taped into one nostril of a patient. The catheter contains a thermistor 13 at its tip. The opposite end of the catheter 17 is connected via a three way valve 18 to positive displacement pump 20. The thermistor 13 is signally connected to a controller 15 via line 14. Completing the system is a rapidly reversing stepper motor 19 which operates pump 29 in either direction thereby directly drawing gas into or forcing gas out of pump 20. The controller is signally connected to stepper motor 19 and valve 18 via lines 24 and 25 and may simultaneously operate both according to a pre-determined control algorithm which is responsive to signals received from thermistor 13. When alveolar gas is to be sampled controller 15 retains valve 18 between pump 29 and catheter 17 in an open position and operates stepper motor 19 in a direction such that a portion of alveolar gas being exhaled through the patient's nostril is withdrawn via catheter 17 into pump 29. At the end of the sampling period, as determined by a present time or when inspiration is detected at thermistor 13, controller 15 instantly reverses stepper motor 19 retining valve 18 in the same position thereby forcing any sampled gas in catheter 17 which may be contaminated by inspired air back through catheter tip 10. When this gas in catheter 17 has been expelled the stepper motor 19 is stopped. This cycle may be repeated several times without emptying pump 10. When the desired amount of alveolar gas has been collected in pump 20, controller 15 actuates valve 18 to close the line between catheter 17 and pump 20 and open a line from pump 20 to tube 23. At the same time stepper motor 19 operates in a direction to force alveolar gas in pump 29 out through tube 23 for collection or directly to an analyzer.

We claim:

1. In a system for sampling alveolar gas exhaled from a subject comprising a non-invasive catheter, signal means for detecting the inspiratory and expiratory phases of the respiratory cycle attached to one end of the catheter, controller means connected with the signal means and valve means located at the other end of the catheter said valve means also being signally connected to and operated by the controller the improvement which comprises (a) a reversible stepper motor connected to and operated by the controller and (b) a positive displacement pump having a pump chamber operated by said stepper motor and connected to said valve means such that alveolar gas may be directly drawn into the pump chamber of said positive displacement pump through said catheter and valve means when the stepper motor is operated in one direction by the controller and discharged from said positive displacement pump chamber through said valve means when the stepper motor is operated in the opposite direction by the controller.

2. In a method for the sampling of alveolar gas exhaled from the airway of a subject through a non-invasive catheter the improvement comprising directly drawing the exhaled alveolar gas through the catheter into the chamber of a positive displacement pump said pump being operated by a reversible stepper motor and discharging the gas collected in said pump chamber to gas collecting means by reversing the direction in which the stepper motor is operated.

3. A method according to claim 2 wherein the pump chamber of the positive displacement pump is interconnected to the non-invasive catheter and gas collecting means through a valve.

4. A method according to claim 3 wherein alveolar gas is drawn through the non-invasive catheter into the pump chamber over a plurality of respiratory cycles before the gas in the pump chamber is discharged.

* * * * *